United States Patent
Xu et al.

(10) Patent No.: US 10,058,699 B2
(45) Date of Patent: Aug. 28, 2018

(54) IMPLANTABLE LEADS WITH FLAG EXTENSIONS

(71) Applicant: Advanced Bionics AG, Staefa (CH)

(72) Inventors: Bing Xu, Valencia, CA (US); Kurt J. Koester, Los Angeles, CA (US); Mark B. Downing, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 13 days.

(21) Appl. No.: 14/911,702

(22) PCT Filed: Aug. 27, 2013

(86) PCT No.: PCT/US2013/056910
§ 371 (c)(1),
(2) Date: Feb. 11, 2016

(87) PCT Pub. No.: WO2015/030739
PCT Pub. Date: Mar. 5, 2015

(65) Prior Publication Data
US 2016/0199638 A1   Jul. 14, 2016

(51) Int. Cl.
*A61N 1/05*   (2006.01)
*A61N 1/36*   (2006.01)

(52) U.S. Cl.
CPC ....... *A61N 1/0541* (2013.01); *A61N 1/36036* (2017.08)

(58) Field of Classification Search
CPC .................................................. A61N 1/36032
See application file for complete search history.

(56) References Cited

U.S. PATENT DOCUMENTS

| 3,752,939 A | 8/1973 | Bartz |
| 4,261,372 A | 4/1981 | Hansen |
(Continued)

FOREIGN PATENT DOCUMENTS

| EP | 2286871 A2 | 2/2011 |
| EP | 2298408 A2 | 3/2011 |
(Continued)

OTHER PUBLICATIONS

Ruddy, et al. "Influence of materials and geometry on fields produced by cochlear electrode arrays", Medical & Biological Engineering & Computing, 1995, 793-801, 33.
(Continued)

*Primary Examiner* — Joseph Dietrich
(74) *Attorney, Agent, or Firm* — Fabian Vancott; Steven L. Nichols

(57) ABSTRACT

In one example, an implantable lead includes a substrate and an electrically conductive material disposed on the substrate to form a flexible circuit. The flexible circuit includes a proximal end adapted to electrically connect to an implantable processor, a distal portion adapted to stimulate a cochlear nerve, and a lead body extending from the proximal end to the distal portion, the lead body having a longitudinal axis and comprising a plurality of electrical traces adapted to carry electrical signals from the proximal end to the distal portion. A flag extension is formed in the substrate and extends laterally outward from the lead body longitudinal axis. A method for forming a cochlear lead with a flag extension is also provided.

19 Claims, 13 Drawing Sheets

(56) References Cited

U.S. PATENT DOCUMENTS

| | | | |
|---|---|---|---|
| 4,284,085 A | 8/1981 | Hansen | |
| 4,502,492 A | 3/1985 | Bornzin | |
| 4,762,135 A | 8/1988 | Van Der Puije | |
| 4,827,932 A | 5/1989 | Ideker | |
| 4,938,231 A | 7/1990 | Milijasevic | |
| 5,042,463 A | 8/1991 | Lekholm | |
| 5,344,387 A | 9/1994 | Lupin | |
| 5,454,370 A | 10/1995 | Avitall | |
| 5,649,970 A | 7/1997 | Loeb | |
| 6,074,422 A | 6/2000 | Berrang | |
| 6,304,787 B1 | 10/2001 | Kuzma | |
| 6,309,410 B1 | 10/2001 | Kuzma | |
| 6,374,143 B1 | 4/2002 | Berrang | |
| 6,546,292 B1 | 4/2003 | Steinhaus | |
| 6,779,257 B2 | 8/2004 | Kiepen | |
| 6,889,094 B1 | 5/2005 | Kuzma | |
| 7,326,649 B2 | 2/2008 | Rodger | |
| 7,706,888 B2 | 4/2010 | Jolly | |
| 7,983,768 B2 | 7/2011 | Dadd | |
| 8,000,798 B2 | 8/2011 | Gantz | |
| 8,014,878 B2 | 9/2011 | Greenberg | |
| 8,126,564 B2 | 2/2012 | Gantz | |
| 8,180,460 B2 | 5/2012 | Neysmith | |
| 8,190,271 B2 | 5/2012 | Overstreet | |
| 8,250,745 B1 | 8/2012 | Orinski | |
| 8,332,052 B1 | 12/2012 | Orinski | |
| 8,880,193 B1 | 11/2014 | Thenuwara | |
| 9,056,196 B2 | 6/2015 | Thenuwara | |
| 9,211,403 B2 | 12/2015 | Tortonese | |
| 2002/0019669 A1* | 2/2002 | Berrang | A61N 1/36036 623/10 |
| 2005/0038489 A1 | 2/2005 | Grill | |
| 2005/0256561 A1 | 11/2005 | Gantz | |
| 2006/0074460 A1 | 4/2006 | Maghribi | |
| 2006/0116743 A1 | 6/2006 | Gibson | |
| 2006/0247754 A1 | 11/2006 | Greenberg | |
| 2006/0259112 A1 | 11/2006 | Greenberg | |
| 2007/0112402 A1 | 5/2007 | Grill | |
| 2007/0179566 A1 | 8/2007 | Gantz | |
| 2007/0203557 A1 | 8/2007 | Gantz | |
| 2007/0251082 A1 | 11/2007 | Milojevic | |
| 2007/0293749 A1 | 12/2007 | Zhou | |
| 2008/0015669 A1 | 1/2008 | Jolly | |
| 2008/0019518 A1 | 1/2008 | Mito | |
| 2008/0057179 A1 | 3/2008 | Greenberg | |
| 2008/0064946 A1 | 3/2008 | Greenberg | |
| 2008/0195178 A1 | 8/2008 | Kuzma | |
| 2008/0234793 A1 | 9/2008 | Gibson | |
| 2008/0288036 A1 | 11/2008 | Greenberg | |
| 2008/0288037 A1 | 11/2008 | Neysmith | |
| 2008/0312717 A1 | 12/2008 | Gantz | |
| 2009/0030483 A1 | 1/2009 | Risi | |
| 2009/0143848 A1 | 6/2009 | Greenberg | |
| 2009/0306745 A1 | 12/2009 | Parker | |
| 2010/0106134 A1 | 4/2010 | Jolly | |
| 2010/0168830 A1 | 7/2010 | Hung | |
| 2010/0204768 A1 | 8/2010 | Jolly | |
| 2011/0202120 A1 | 8/2011 | Ball | |
| 2011/0264168 A1 | 10/2011 | Dadd | |
| 2011/0301665 A1 | 12/2011 | Mercanzini | |
| 2011/0319907 A1 | 12/2011 | Gallegos | |
| 2012/0004715 A1 | 1/2012 | Ramachandran | |
| 2012/0158113 A1 | 6/2012 | Jolly | |
| 2012/0192416 A1 | 8/2012 | Neysmith | |
| 2014/0303703 A1 | 10/2014 | Mercanzini | |
| 2014/0336739 A1 | 11/2014 | Loth | |
| 2015/0267314 A1 | 9/2015 | Thenuwara | |
| 2015/0320550 A1 | 11/2015 | Downing | |

FOREIGN PATENT DOCUMENTS

| | | |
|---|---|---|
| WO | 0112115 | 2/2001 |
| WO | 2008011721 A9 | 1/2008 |
| WO | 2009062114 A2 | 5/2009 |
| WO | 2009121110 | 10/2009 |
| WO | 2010055421 | 5/2010 |
| WO | 2011075480 | 6/2011 |
| WO | 2012003295 A1 | 1/2012 |
| WO | 2012003297 A1 | 1/2012 |
| WO | 2012034162 A2 | 3/2012 |
| WO | 2012154256 | 11/2012 |
| WO | 20140105059 A1 | 12/2012 |
| WO | 2013048396 A1 | 4/2013 |
| WO | 2013103489 | 7/2013 |
| WO | 2015023280 | 2/2015 |
| WO | 2015030734 | 3/2015 |

OTHER PUBLICATIONS

Wei, et al.; "Analysis of high-perimeter planar electrodes for efficient neural stimulation"; Frontiers in Neuroengineering; Nov. 2009; vol. 2.

Wei, Xuefeng Frank; "Analysis and Design of Electrodes for Deep Brain Stimulation"; Doctoral Thesis; Dept. of Biomedical Engineering; Duke University; 2009.

\* cited by examiner

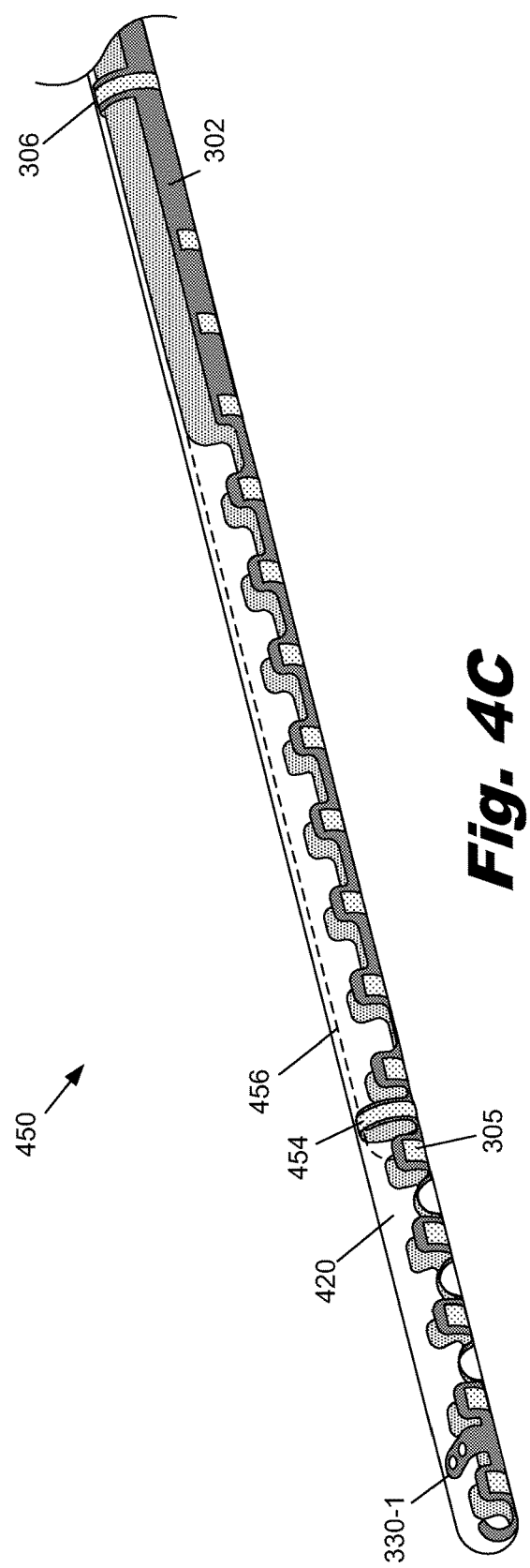

Section B-B

IMPLANTABLE LEADS WITH FLAG EXTENSIONS

BACKGROUND

Neurostimulating devices stimulate nerves by applying an electrical current. Such devices often include a biocompatible implantable lead that carries current from a pulse generator or Radio Frequency (RF) link to the stimulation site. These implantable leads can include multiple small diameter wires and are typically constructed manually. Manually handling the wires is laborious and requires skilled technicians. This manual assembly process can result in significant variation in the spacing and organization of the wires that make up the implantable lead. This can result in undesired variations in the geometry and properties within and between implantable leads. Additionally, the manual manufacturing can be expensive because it is a low yield and a low throughput process.

BRIEF DESCRIPTION OF THE DRAWINGS

The accompanying drawings illustrate various examples of the principles described herein and are a part of the specification. The illustrated examples are merely examples and do not limit the scope of the claims.

FIG. 4C is a perspective view of an implantable lead with flag extensions, according to one example of principles described herein.

Throughout the drawings, identical reference numbers designate similar, but not necessarily identical, elements.

DETAILED DESCRIPTION

Neurostimulating devices find wide spread use to compensate for deficient or malfunctioning biological structures or systems. For example neurostimulating devices can be effectively used to improve the function of auditory, visual, and central nervous systems. These neurostimulating devices include an implantable lead that includes a number of electrodes and wires connected to those electrodes. The implantable lead allows the electrodes to be placed in proximity to the desired nerves. A current source is typically placed in a more accessible area that is away from the nerves. The current source is connected to the electrodes by the wires in the implantable lead. Construction of the implantable leads can be challenging. The wires and electrodes are often very small and are typically constructed manually. Manually handling the wires is laborious and requires skilled technicians. This manual assembly process can result in significant variation in the spacing and organization of the wires that make up the implantable lead. This can result in undesired variations in the geometry and properties within and between implantable devices. Additionally, the manual manufacturing can be expensive because it is a low yield and a low throughput process.

In the following description, for purposes of explanation, numerous specific details are set forth in order to provide a thorough understanding of the present systems and methods. It will be apparent, however, to one skilled in the art that the present apparatus, systems and methods may be practiced without these specific details. Reference in the specification to "an example" or similar language means that a particular feature, structure, or characteristic described in connection with the example is included in at least that one example, but not necessarily in other examples. Features shown and/or described in connection with one figure may be combined with features shown and/or described in connection with other figures.

Figure 1:
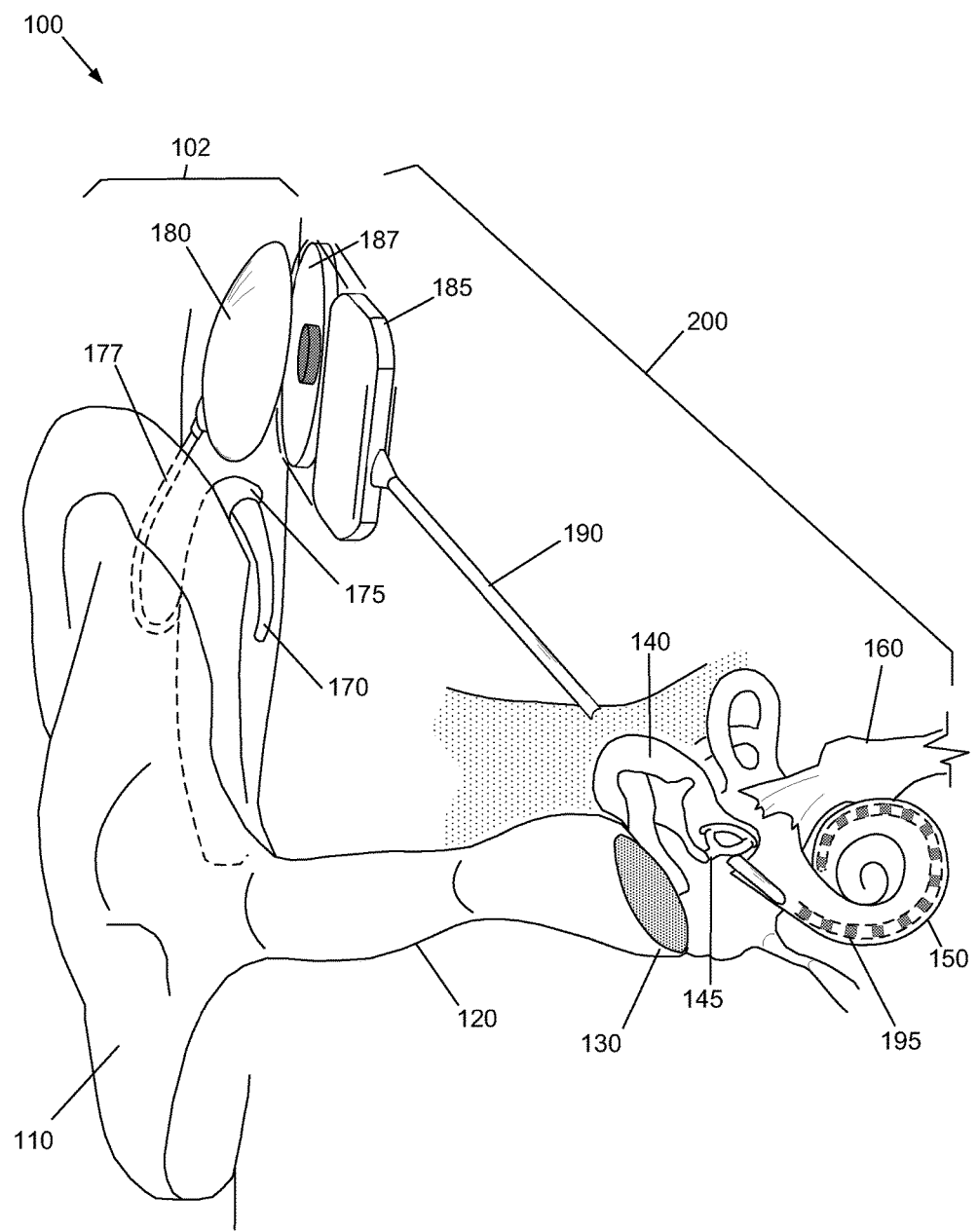
FIG. 1 shows a cochlear implant system in use by a patient, according to one example of principles described herein.

FIG. 1 is a diagram showing one illustrative example of a neurostimulating cochlear implant system (100) that includes an internal implanted portion (200) and an external portion (102). In a functioning human ear, sound enters the external ear (110) and passes through the ear canal (120) to the ear drum (130). A series of three small bones (145) in the middle ear (140) amplify the motion of the ear drum and transmit the amplified signals to the cochlea (150). Fluid inside the cochlea (150) moves in response to the amplified signals. Hair cells in the cochlea (150) convert the motion of the fluid into nerve impulses that travel through the auditory nerve (160) to the brain.

The cochlear implant system (100) provides a sense of sound to a person who is profoundly deaf or severely hard of hearing. In many cases, deafness is caused by the absence or destruction of the hair cells in the cochlea, i.e., sensorineural hearing loss. In the absence of properly functioning hair cells, there is no way auditory nerve impulses can be directly generated from ambient sound. Thus, conventional hearing aids, which amplify external sound waves, provide no benefit to persons suffering from complete sensorineural hearing loss.

Figure 2A:
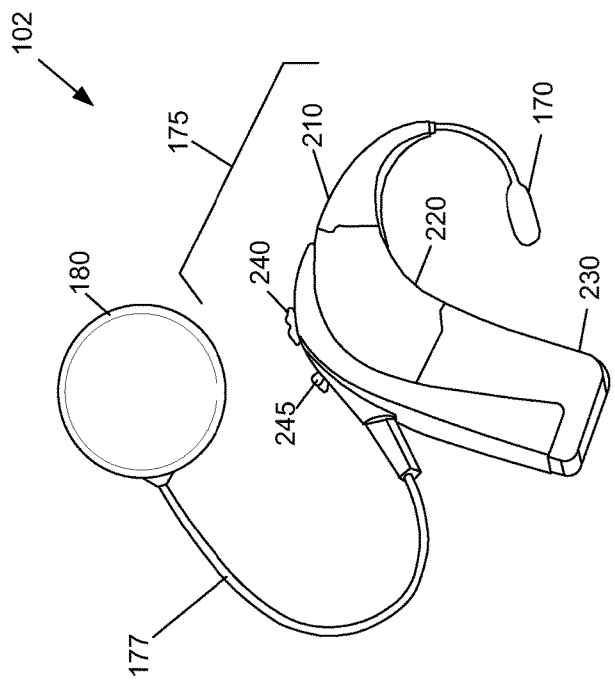
FIGS. 2A and 2B show the external and internal portions of a cochlear implant system, respectively, according to one example of principles described herein.

The external portion (102) of the cochlear implant system (100) can include a. Behind-The-Ear (BTE) unit (175) that contains the sound processor and has a microphone (170), a cable (177), and a transmitter (180). The microphone (170) picks up sound from the environment and converts it into electrical impulses. The sound processor within the BTE unit (175) selectively filters and manipulates the electrical impulses and sends the processed electrical signals through the cable (177) to the transmitter (180). The transmitter (180) receives the processed electrical signals from the BTE unit (175) and transmits them to the implanted antenna assembly (187) by electromagnetic transmission. FIG. 2A shows the external portion (102) of the cochlear implant system, including the BTE unit (175), battery (230), processor (220), ear hook (210), and microphone (170). A number of controls (240, 245) are located on the processor (220). These controls may include an on/off switch (245) and volume switch (240). The cable (177) connects the processor (220) to the transmitter (180).

Figure 2B:
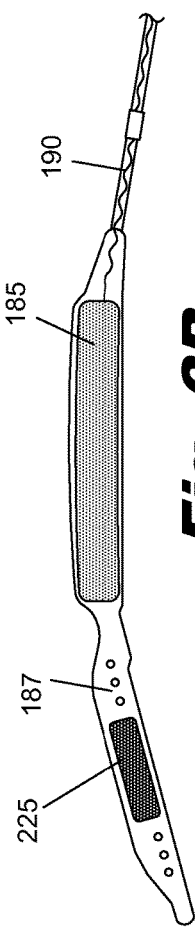

The internal implanted portion (200) of the cochlear implant system shown in FIG. 2B includes an electrode array (195) that is surgically placed within the patient's cochlea. Unlike hearing aids, the cochlear implant system (100, FIG. 1) does not amplify sound, but works by directly stimulating any functioning auditory nerve cells inside the cochlea (150, FIG. 1) with electrical impulses representing the ambient acoustic sound. This bypasses the defective cochlear hair cells that normally transduce acoustic energy into electrical energy. The implanted portion (200) of the cochlear implant system is shown in FIG. 1 in its implanted configuration and in FIG. 2B before implantation. The implanted portion (200) of the cochlear implant (100, FIG. 1) includes an internal processor (185), an antenna assembly (187), and an implantable lead (192). The implantable lead (192) includes a lead body (190) and an electrode array (195). The internal processor (185) and antenna assembly (187) are secured beneath the user's skin, typically above and behind the external ear (110, FIG. 1). The antenna assembly (187) receives signals and power from the transmitter (180, FIG. 1, FIG. 2A). The internal processor (185) receives these signals and operates on the signals to generate modified signals. These modified signals are then sent through the lead body (190) to the electrode array (195), which is at the distal portion of the implantable lead (192) and is implanted within the cochlea (150, FIG. 1). The electrode array (195) uses the modified signals to provide electrical stimulation to the auditory nerve (160).

FIG. 2B is a side view of the implanted portion (200) of a cochlear implant (100, FIG. 1). The implanted portion (200) includes the antenna assembly (187) and the internal processor (185). In this example, the antenna assembly (187) is external from the internal processor (185). A magnet (225) is disposed in the center of the antenna assembly (187). The magnet (225) removably secures the transmitter (180, FIG. 1) over the antenna assembly (187). The antenna assembly (187) is connected to the internal processor (185). The implantable lead (192) is connected to the opposite side of the internal processor (185).

Figure 3A:
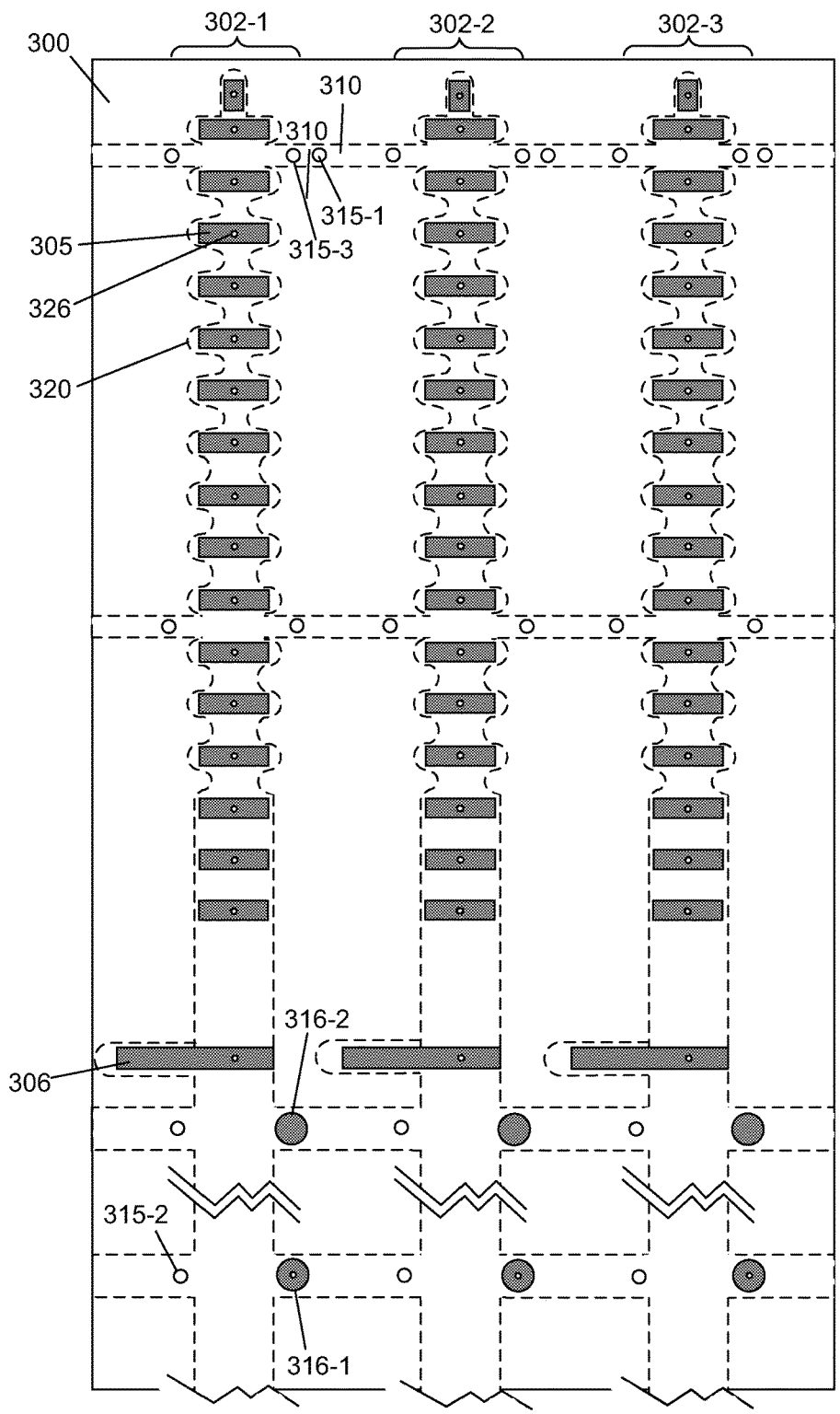
FIG. 3A is a planar view of a circuit substrate with electrodes formed thereon, according to one example of principles described herein.

FIG. 3A shows a circuit substrate (300) upon which three implantable circuits (302-1, 302-2, 302-3) will be formed. The circuit substrate (300) may be any of a number of materials, including flexible non-thermoformable material and/or a thermoplastic material. A number of electrodes (305, 306) are formed on the upper face of the circuit substrate (300). These electrodes (305, 306) may include stimulating electrodes (305), ring electrodes (306), and other electrodes. In this example, the electrodes have through holes (326) that pass through the electrode and the substrate. These through holes (326) will later be used to form vias to connect traces that will be formed on the opposite side of the substrate (300) to the electrodes (305).

The dashed outlines (320) show where the implantable circuits (302) will subsequently be cut out of the circuit substrate (300). In the example shown in FIG. 3A, there are three implantable circuits (302-1, 302-2, and 302-3) laid out together. The nesting of these implantable circuits together on the same substrates allows for multiple electrode arrays to be formed at the same time. This can increase efficiency in the production of the implantable circuits by reducing handling and fixturing times. The combination of two or more implantable circuits that are formed in a single sheet is called a "tray" of implantable circuits. In the example shown in FIGS. 3A and 3B, there are only three implantable circuits in the tray. However, any number of implantable circuits may be included on the tray and formed simultaneously during the processing steps. The implantable circuits (302) are connected by extensions (310) that extend on either side of the implantable circuits (302). When the implantable circuits (302) are cut out of the substrate in a subsequent operation, they will still be connected by the extensions (310). In this example, the extensions include a number of apertures (315), electrodes (316) and other features. When the implantable circuits (302) are separated, the extensions (310) can be formed into flag extensions or cut entirely from the implantable circuits (302). These flag extensions may serve a number of purposes as described below.

Figure 3B:
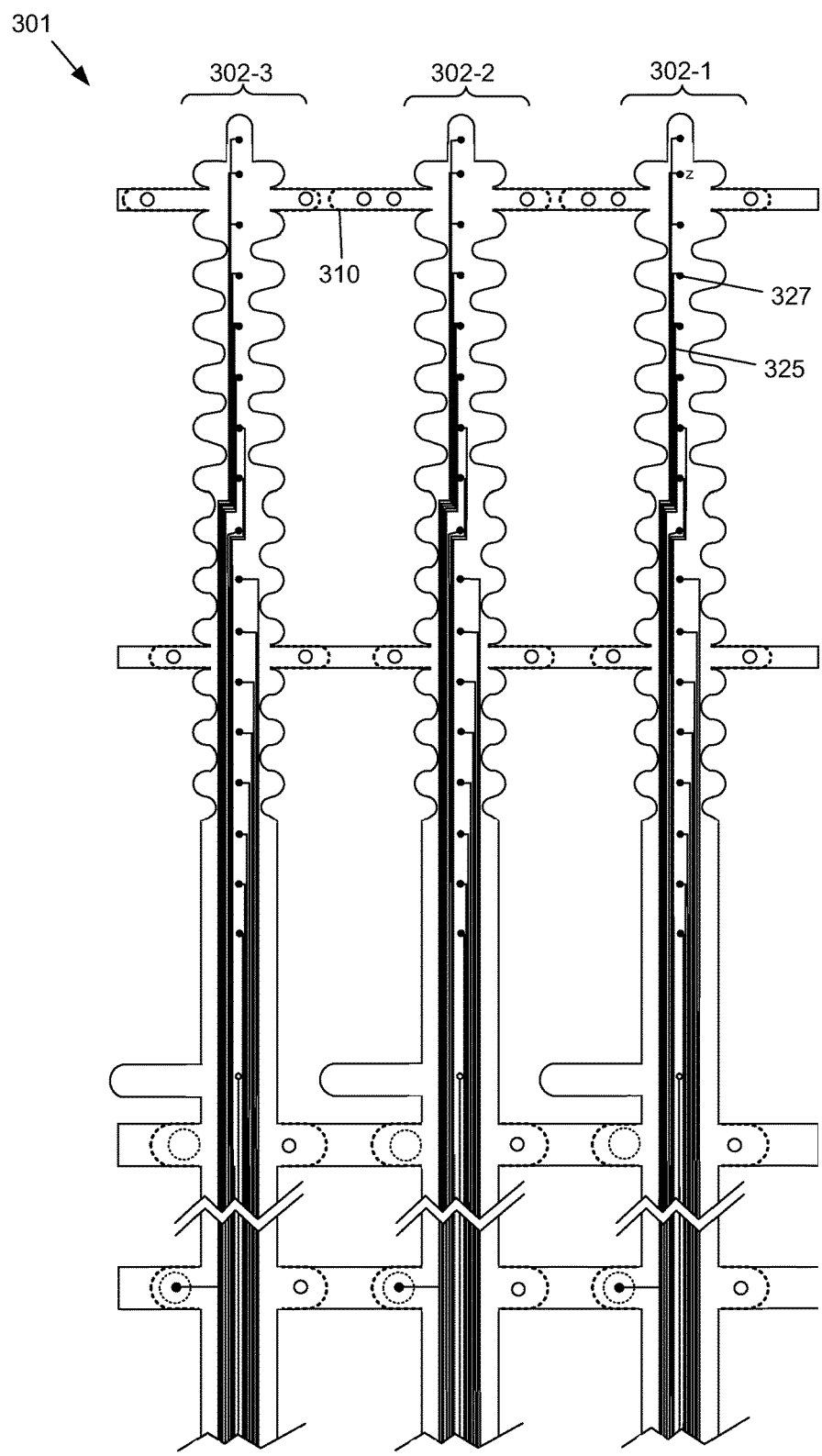
FIG. 3B is another view of substrate of FIG. 3A with traces and vias formed on the circuit substrate, according to one example of principles described herein.

In FIG. 3B, the circuit substrate has been flipped around a vertical axis to show the opposite side of the substrate. In this step of the manufacturing process, a number of traces (325) are formed. During the formation of the traces (325) (or during the formation of the electrodes), the holes (326, FIG. 3A) are filled to form vias (327). These vias (327) connect traces (325) on the back side of the circuit substrate (300) to the electrodes on the front side of the circuit substrate (300). The electrodes, traces, and vias can be formed from any appropriate material using any appropriate process. For example, the material may be a biologically compatible conductive metal such as gold, platinum, iridium or alloys thereof. The traces, electrode and vias can be formed using a number of processes, including printing processes, lithography, vacuum deposition, electroplating, etching, etc. In some examples, the conductive elements on the substrate may be formed using a combination of processes. For example, the traces may be initially formed using a lithographic process and then thickened using an electroplating process.

FIG. 3B also shows that the circuit substrate has been cut to remove portions of the substrate that are not part of the circuits. This forms the circuit tray (301) with the individual implantable circuits (302) connected by the extensions (310). In this example, there are at least four extensions (310) connecting the implantable circuits (302). The number of extensions (310) can be more or less depending on the specific application, the number of desired flag extensions, and the amount of desired connectivity between the implantable circuits (310).

Figure 3C:
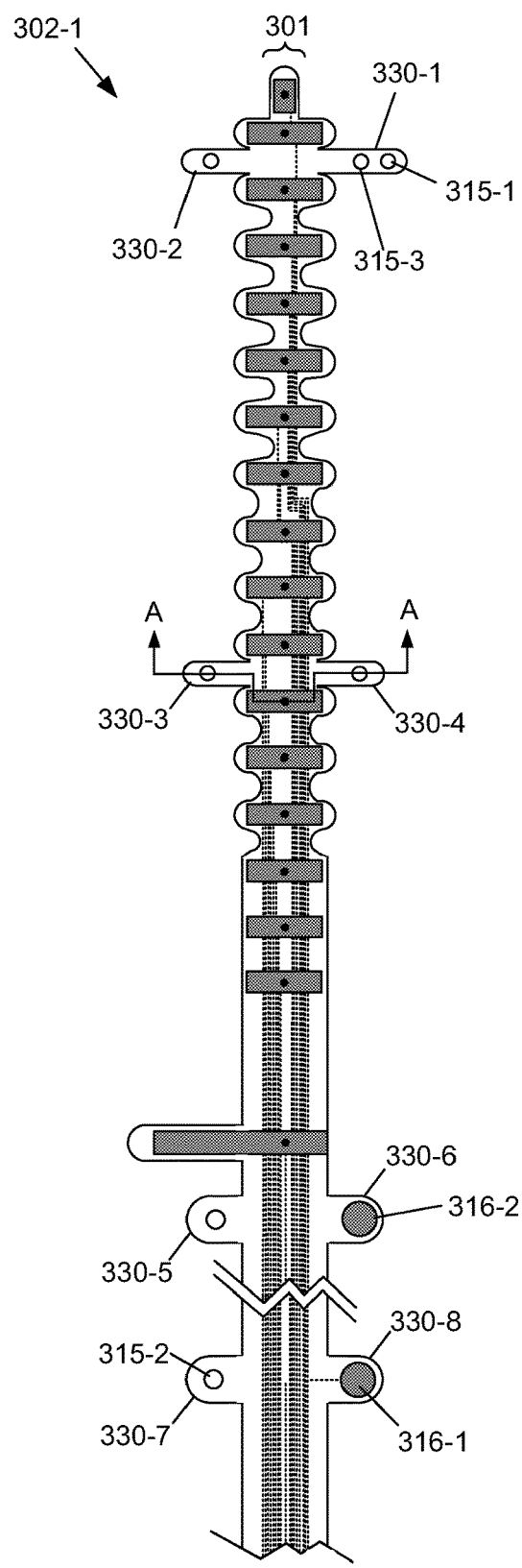
FIG. 3C is a diagram of a circuit with flag extensions, according to one example of principles described herein.
Figure 6A:
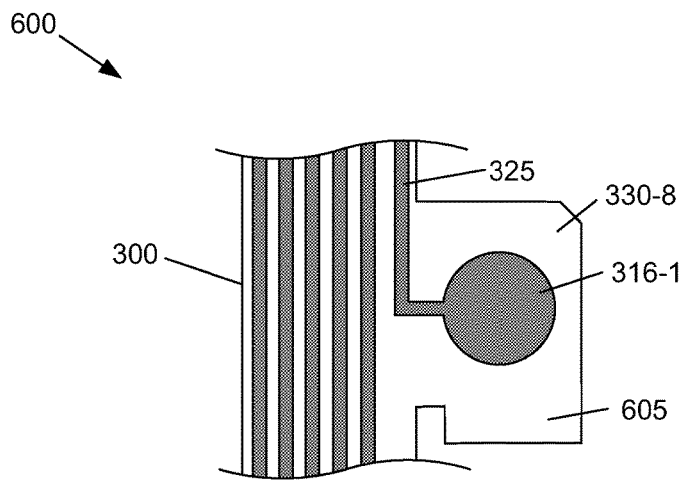
FIGS. 6A-6C are cross sectional diagrams of an implantable lead with flag extensions used as a connection pad for a ring electrode, according to one example of principles described herein.
Figure 6B:
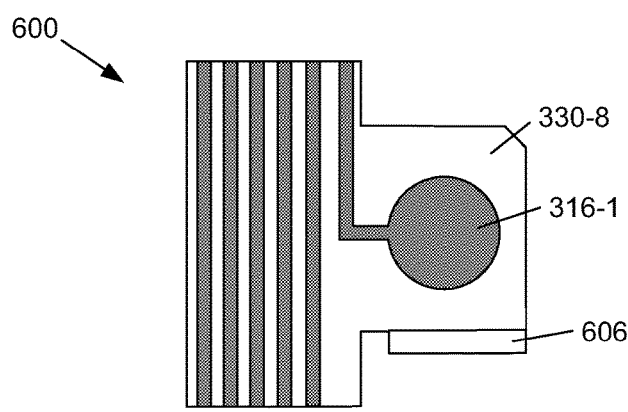
Figure 6C:
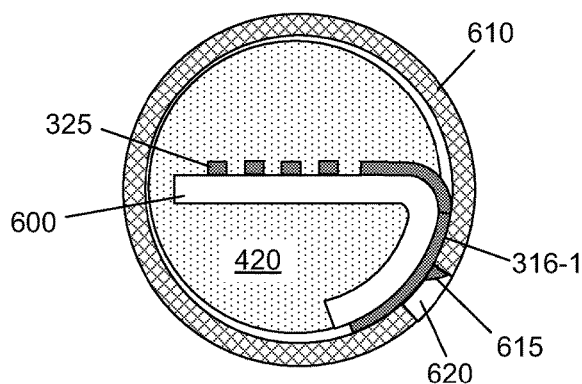
Figure 7A:
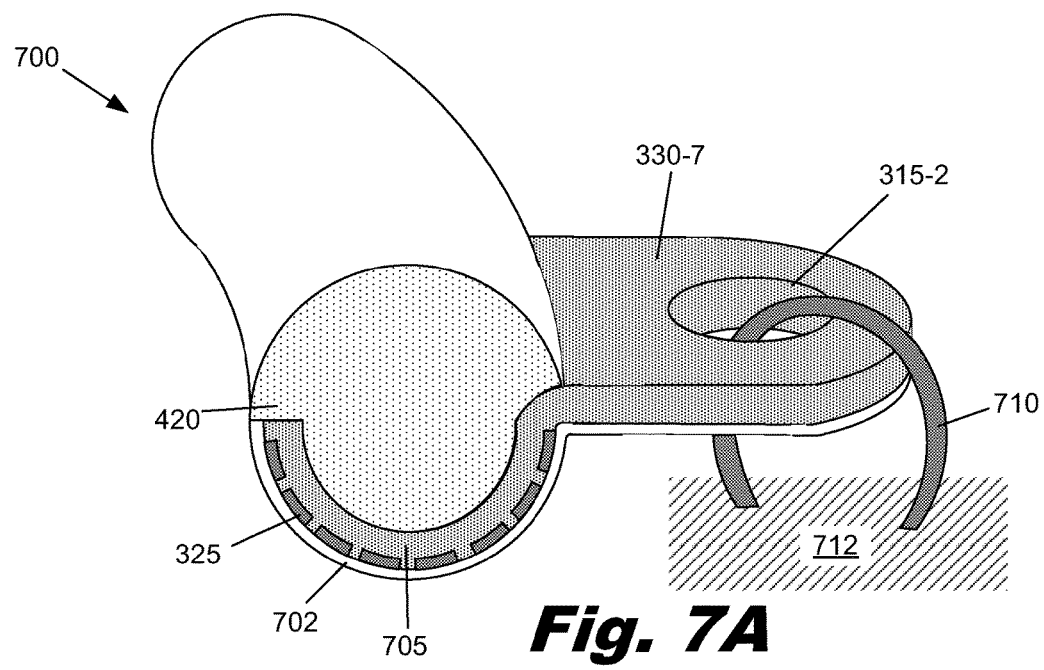
FIGS. 7A and 7B are diagrams of an implantable lead with flag extensions used as suture attachments, according to one example of principles described herein.
Figure 7B:
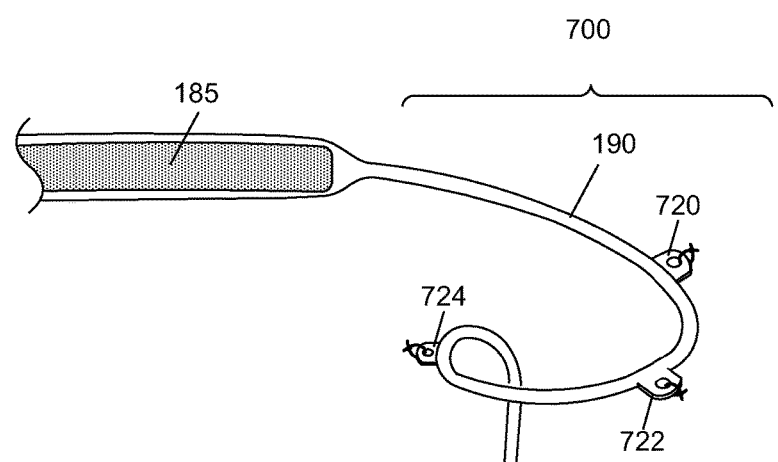
Figure 8:
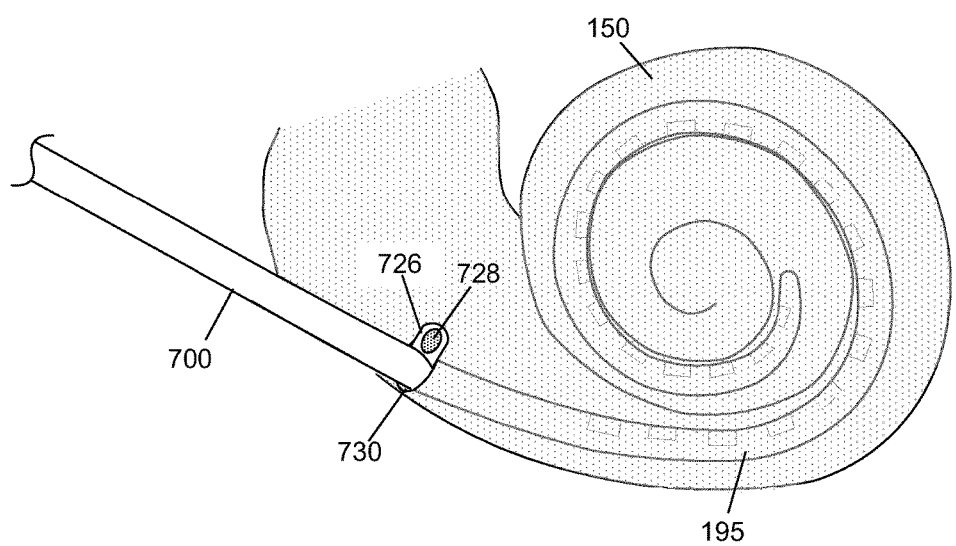
FIG. 8 shows an implantable lead with a flag extension inserted into a cochlea, according to one example of principles described herein.
Figure 9A:
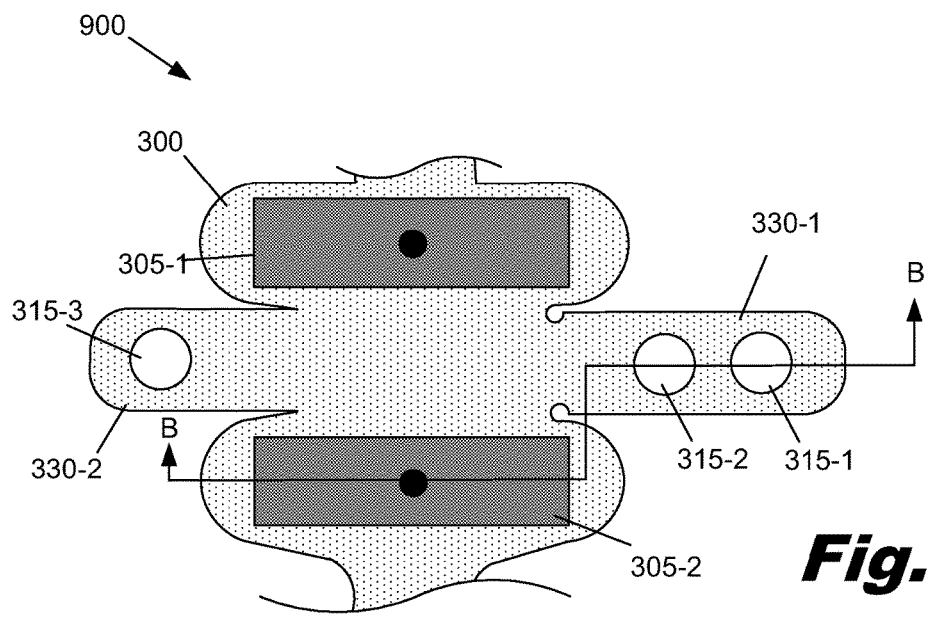
FIGS. 9A and 9B are diagrams of a circuit and implantable lead with a flag extension that is mechanically overlocked within flexible encapsulation, according to one example of principles described herein.
Figure 9B:
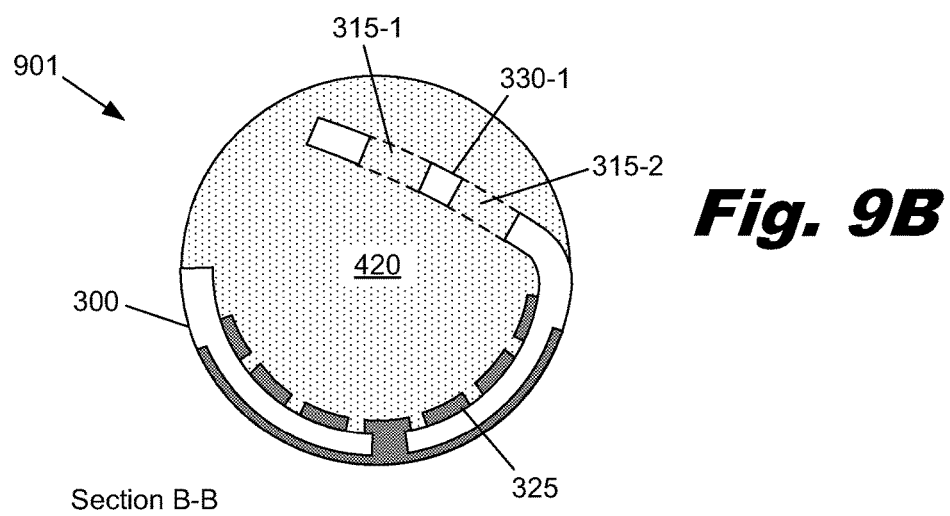

FIG. 3C shows an implantable circuit (302-1) for a cochlear lead that has been separated from the tray (301, FIG. 3B) by cutting the extensions (310, FIG. 3A). The extensions (310, FIG. 3B) then become flag extensions (330) that extend outward from the central body (301) of the implantable circuit (302-1). The flag extensions (330) are integral parts of the circuit (302-1) and are formed out of the circuit substrate (300, FIG. 3A). In this example, there are eight flag extensions (330-1 through 330-8). A first flag extension (330-1) includes two apertures (315-1, 315-3) and, as discussed below, is used for alignment and for mechanical overlocking. This is illustrated in FIGS. 9A and 9B. The second, third, and fourth flag extensions (330-2, 330-3, 330-4) include through apertures (e.g. 315-2) that are used for alignment during subsequent operations (see FIGS. 4A and 4B). These flag extensions are removed from the cochlear lead after their alignment functions have been performed. The fifth and seventh flag extensions (330-5, 330-7) are used both for alignment and as an anchor point for the cochlear lead. This is illustrated in FIGS. 7A and 7B. The sixth flag extension does not have a through aperture but includes a marker electrode (316-2). As discussed below in FIG. 7B and FIG. 8 the marker electrode allows a surgeon to visually determine a correct insertion depth of the cochlear electrode array into the tissue. The eighth flag extension (330-8) includes an electrode (316-1) connected to a trace (325, FIG. 3B). The electrode (316-1) serves as a contact pad for a subsequently attached ring electrode as shown in FIG. 6A-6C.

For purposes of illustration, only a few examples of flag extensions are shown. A cochlear lead or other implantable lead may include a variety of different flag extensions. For example, the flag extensions are shown extending from the main body between adjacent electrodes. However, the flag extensions could extend from the ends of the electrodes. This and other principles related to circuits that form implantable leads are discussed in International App. No. PCT/US2013/056875, entitled "Thermoformed Electrode Array," to Bing Xu et al., filed Aug. 27, 2013 which published as International Pat. Pub. No. WO2015030734 on Mar. 5, 2015, which is incorporated herein by reference in its entirety. Additionally, there may be more or less flag extensions in a given design. For example, in some designs there may be flag extensions that extend from both ends of each stimulating electrode that are used to mechanically overlook the electrode into a flexible body.

Figure 4A:
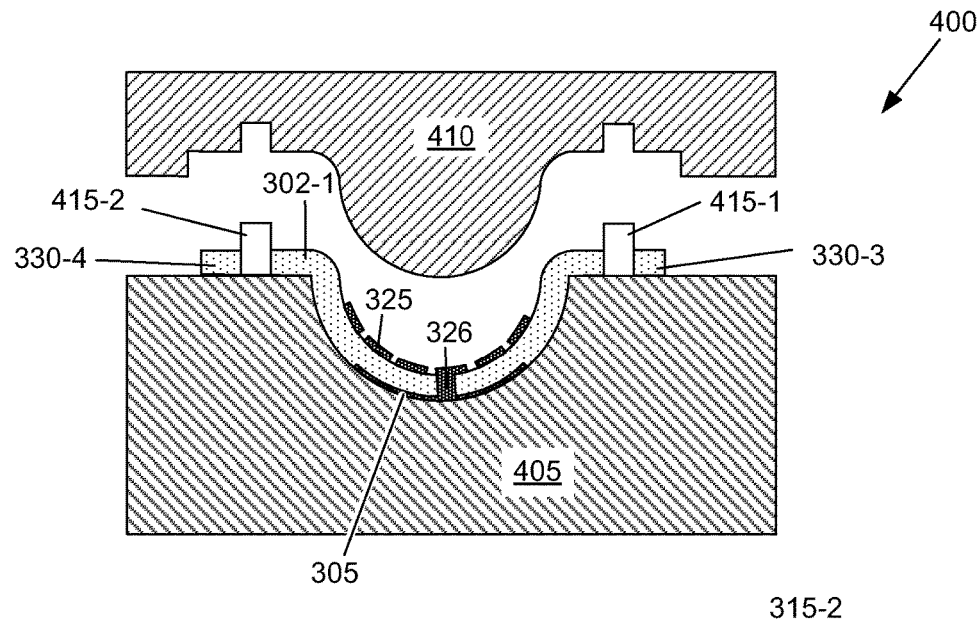
FIG. 4A is a cross sectional diagram of a circuit with flag extensions in a thermoforming mold, according to one example of principles described herein.

FIG. 4A shows the implantable circuit (302-1) placed in a thermoforming mold (405, 410). The view of the circuit (302-1) is taken along the section line A-A shown in FIG. 3C. In this example, the circuit (302-1) includes a thermoplastic that can be formed into a predetermined shape through the application of heat and pressure. The thermoforming mold includes a lower mold (405) and a mating upper mold (410). The circuit (302-1) is aligned to the lower mold (405) by placing apertures in the flag extensions (330-3, 330-4) over pins (415) protruding from the lower mold (405). The molds (405, 410) and circuit (302-1) are heated to a desired temperature and the upper mold (410) is pressed down into the lower mold (405). This forms the circuit (302-1) into the desired shape.

During this process, the circuit (302-1) is secured by the pins (415) passing through apertures in the flag extensions (330-3, 330-4). In some implementations, the heating of the circuit (302-1) is not uniform. For example, the center portion of the circuit (302-1) containing the traces (325), vias (327) and electrodes (305) may be heated while the flag extensions (330-3, 330-4) are not heated or are heated to a much lower temperature. In one implantation, the center portion of the circuit (302-1) may be heated above the glass transition temperature of the thermoplastic, while the flag extensions (330-3, 330-4) are not heated above the glass transition temperature. Thus, when the upper mold (410) is brought down into the lower mold (405), the center portion of the circuit (302-1) deforms while the flag extensions (330-3, 330-4) remain more dimensionally stable. The circuit (302-1) is then cooled below the glass transition temperature and removed from the thermoforming mold (405, 410) by pulling the circuit (302-1) upward to withdraw the pins (415) from the apertures in the flag extensions (330-3, 330-4). The circuit (302-1) then retains its thermoformed shape.

The steps and structures described above are only one example for thermoforming a circuit. A variety of other structures and methods could be used. For example, the pins could be any of a variety of alignment features and the apertures could have a variety of shapes. Additionally the steps described above could be reordered, combined, deleted, or new steps could be added. For example, the mold may be closed it is heated.

Figure 4B:
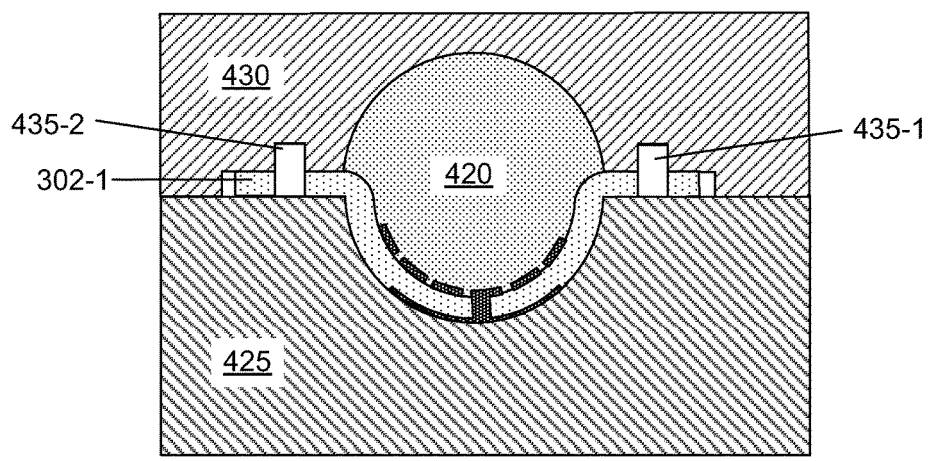
FIG. 4B is a cross sectional diagram of a circuit with flag extensions in a liquid injection mold, according to one example of principles described herein.

FIG. 4B shows the thermoformed circuit (302-1) placed into a liquid injection mold (425, 430). The liquid injection mold includes a lower mold (425) with pins (435-2) that fit into the alignment apertures in the flag extensions. This secures the thermoformed circuit (302-1) in place. The upper mold (430) is secured over the lower mold (425), creating a cavity that is filled with a flexible encapsulant such as silicone to form a flexible body (420). The combination of the flexible body (420) and the thermoformed circuit (302-1) form an implantable lead. The circuit (302-1) provides the electrical functions of the implantable lead and the flexible body (420) improves the mechanical characteristics of the implantable lead. For example, the flexible body (420) smooths the contours of the circuit (302-1) to eliminate edges and corners that may cause tissue irritation. The flexible body (420) may also reduce the tendency of the implantable lead to kink during insertion.

FIG. 4C shows a perspective view of an implantable lead (450) that includes a thermoformed circuit (302) with flag extensions (330-1, 454, 306) joined to a flexible body (420). A number of stimulating electrodes (305) are arranged in a linear array along the length of the implantable lead (450). The thermoformed circuit (302) is similar to those shown in FIGS. 3A-3C, but not identical. A first flag extension (330-1) has been retained on the thermoformed circuit (302) and extends into the interior of the flexible body (420) to more securely retain the thermoformed circuit (302) in place in the flexible body (420). The second and third flags (454, 306) have been thermoformed into ring electrodes/markers that pass around the perimeter of the implantable lead (450). These ring electrodes/markers may serve a number of purposes including acting as ground electrodes or insertion depth markers. In this example, a lumen (456) extends axially through a portion of the implantable lead (450). The lumen (456) may be configured to receive a stylet. The stylet may be part of a surgical implantation system and provide additional rigidity to the implantable lead (450) during the insertion of the lead (450) into the cochlea.

The discussion and illustrations above are only illustrative examples of implantable leads that include flag extensions. A variety of other configurations and materials could be used. For example, the circuit may not include thermoplastic, but may be formed on a flexible non-thermoformable flexible substrate. For example, the circuit may include both a flexible non thermoformable layer and a thermoplastic thermoformable layer.

The flexible encapsulant may then be formed around the flexible substrate to hold it in the desired shape. In other implementations, the circuit may include a number of sub-layers that are bonded together. For example the circuit may include both a flexible layer and a thermoplastic layer. A variety of these configurations are illustrated in International App. No. PCT/US2013/056875, entitled "Thermoformed Electrode Array" to Bing Xu et al., filed Aug. 27, 2013, which published as International Pat. Pub. No. WO2015030734 on Mar. 5, 2015, which was incorporated by reference above.

Figure 5A:
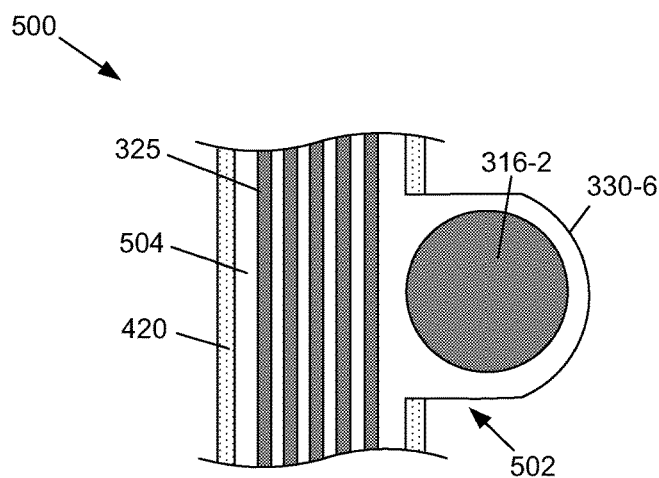
FIGS. 5A-5C are cross sectional diagrams of implantable leads with flag extensions that are used as markers, according to one example of principles described herein.
Figure 5B:
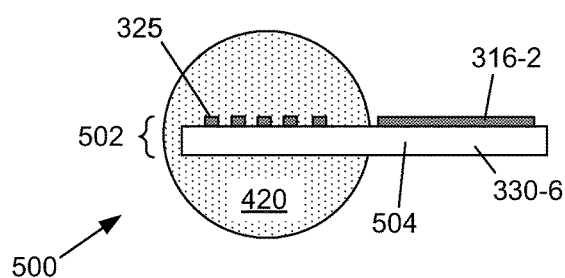

FIGS. 5A and 5B are diagrams of a portion of an illustrative implantable lead (500). In this example, the circuit (502) is not shaped to conform to the outer contours of the flexible body (420). The circuit (502) is flat and includes a substrate (504), a number of traces (325) formed on the substrate (504) and a flag extension (330-6). The flag extension (330-6) has a marker (316-2) formed on one or more of its surfaces. The marker (316-2) may be formed from any of a number of materials. For example, if the marker (316-2) is intended to supply a visual indication of the insertion depth of the implantable lead (500) to a surgeon, the marker (316-2) may be formed from biologically compatible material with distinct visual characteristics. For example, the marker could be formed from textured metal, metal with visually distinct surface treatment, or may include colored dyes.

If the marker is intended to serve as a reference for x-ray imaging, the marker may be formed from radiopaque material. In some circumstances, the visual marker may include both visual and radiopaque characteristics. The radiopaque material could be the same as the trace material or may be different than the trace material. The radiopaque material may be tantalum, platinum, or other biocompatible radiopaque material. The radiopaque material may be disposed in any layer of the substrate, on the substrate or in an encapsulating layer. For example, the radiopaque material may be powered and mixed into a silicone matrix which forms the encapsulant over the flag extension.

FIG. 5B shows that the circuit (502) is flat within this portion of the implantable lead (500). However, the circuit (502) may have a variety of shapes. For example, the circuit (502) may be flat or have a wavy contour in the lead body (190, FIG. 2B) that connects the electrode array (195, FIG. 2B) to the internal processor (185, FIG. 2B). In FIG. 5B, the marker (316-2) is formed on the same side of the circuit substrate (504) as the traces (325). The flag extension (330-6) containing the marker (316-2) extends out of the flexible body (420).

Figure 5C:
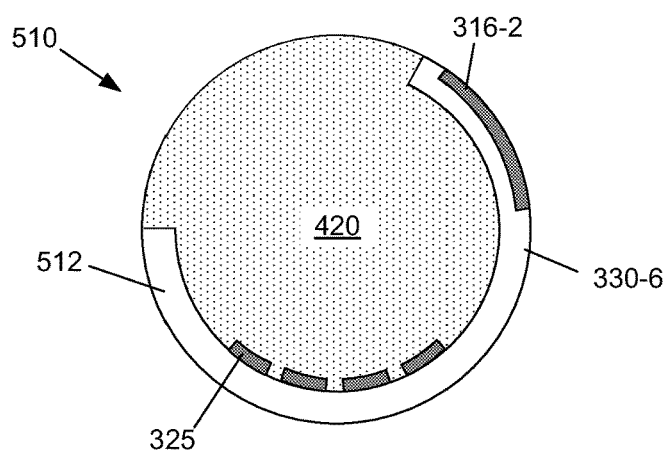

FIG. 5C shows a different cross sectional view of an implantable lead (510), where the circuit (512) is formed to match the outer contours of the flexible body (420). In this example, the marker (316-2) on the flag extension (330-6) is formed on the surface of the circuit (512) that is opposite the traces (325).

FIG. 6A is a diagram of a portion of circuit (600) that includes a substrate (300) with traces (325) formed on at least one surface. A flag extension (330-8) is an integral part of the circuit (600) and extends from one side of the main portion of the circuit (600). The flag extension (330-8) includes a contact pad (316-1) that is electrically connected to a trace (325). The flag extension (330-8) also includes a protrusion (605). The contact pad (316-1) will be used to make electrical contact with an overlying solid body electrode. For example, a ring electrode may be formed from a conductive material and electrically attached to the contact pad (316-1). Electrical signals passed down the trace (325) and are transmitted through the contact pad (316-1) to the ring electrode and into the target biological tissue.

FIG. 6B shows the flag extension (330-8) with the protrusion (605, FIG. 6A) bent upward to form a lip (606). This may be accomplished in a variety of ways, include thermoforming. The lip (606) may act as a stop that positions the ring electrode or other solid body electrode over the contact pad (316-1). For example, the circuit (600) may be thermoformed and encapsulated in a flexible body to form an implantable lead. The lip (606) may extend outward from the flexible body. When a ring electrode is slid over the implantable lead, it will encounter the lip (606) and stop in the desired location over the contact pad (316-1).

FIG. 6C shows the thermoformed circuit (600) encapsulated in a flexible body (420) with the contact pad (316-1) exposed on an outer surface of the flexible body (420). The ring electrode (610) is placed over the flexible body (420) and positioned over the contact pad (316-1). In this example, the ring electrode (610) includes an aperture (620) that exposes a portion of the contact pad (316-1). A weld (615) or other connection is formed in the aperture and electrically connects the contact pad (316-1) and ring electrode (610).

The embodiments given above are only examples. A variety of other configurations could be used. For example, a portion of the contact pad (316-1) may extend to the lip (606) and electrical contact between the ring electrode (610) (or other conductive body) may be formed at the lip.

FIG. 7A is a partially cut away perspective view of a flag extension (330-7) that serves as an anchor point for the implantable lead (700). In this example, the circuit includes two layers, a flexible circuit layer (702) and a thermoplastic layer (705). Traces (325) are formed on a surface of the flexible circuit layer (702) and sandwiched between the flexible circuit layer (702) and the thermoplastic layer (705). The flag extension (330-7) extends away from the flexible body (420) and includes an aperture (315-2). A variety of connections to surrounding biological tissue can be made using the flag extension (330-7), including bone screw attachments and suture attachments. FIG. 7A shows a suture (710) passing through the aperture (315-2) and into the surrounding biological tissue (712). The description above is only one example of a flag extension. A variety of other configurations could be used. For example, a flag extension may also be encapsulated with silicone or other encapsulant.

FIG. 7B shows an internal processor (185) and an implantable lead (700) connected to the internal processor (185). The implantable lead (700) includes three flag extensions (720, 722, 724) that are used as anchor points. In this example, the implantable lead (700) is a cochlear lead and the anchor points are located along the lead body (190). Typically, the lead body (190) is coiled in a recess in the mastoid portion of the temporal bone in the human skull. This coil allows for some amount of differential motion between the internal processor (185) and the electrode array (195) that is implanted in the cochlea (150). Anchoring the lead body (190) with anchor flag extensions (720, 722, 724) and sutures/bone screws preserves the coiled configuration of the lead body (190) while still allowing the desired strain relief.

FIG. 7B also shows a marker flag extension (726) that is designed to visually indicate the correct (or target) insertion depth for the electrode array (195). FIG. 8 shows an enlarged view of the marker flag extension (726). The marker flag extension (726) can be formed in a variety of ways, including those described above. In one example, the marker flag extension (726) is an integral part of a thermoformed circuit. In this implementation, the marker flag extension (726) is formed by thermoforming an extension of the circuit so that it is perpendicular (in a cross-sectional plane) to the main portion of the body. For example, the marker flag extension (726) may be rotated 90 degrees so that it is in a cross sectional plane of the lead (700). In some implementations, the marker flag extension (726) may be overmolded with silicone. This may occur during liquid injection molding or may be applied at a later time.

When the surgeon inserts the electrode array (195) into the cochlea (150) through a cochleostomy (730), the marker flag extension (726) contacts the edge of the cochleostomy, providing the surgeon with a very discernible visual indicator of the maximum insertion depth of the electrode array. The marker flag extension (726) may also provide a mechanical stop that provides tactile feedback to the surgeon at the maximum insertion depth. A marker flag (728) may be placed on the marker flag extension (726) so that the marker flag extension (726) is clearly visible. In some implementations, the marker flag extension (726) may include an aperture configured to receive a bone screw for anchoring the electrode array in place. In other examples, the marker flag extension (726) may be adhered to the outer surface of the cochlea to hold the electrode array in place. The adhesive may be permanent or temporary. For example, a biocompatible adhesive that is designed to hold the electrode array (195) in place for three to four weeks would allow for healing of the surgically disturbed tissue to stabilize the cochlear implant.

FIGS. 9A and 9B show a circuit (900) with a flag extension (330-1) that is thermoformed into the interior of the flexible body (420) so that the flexible body (420) mechanically overlooks the circuit (900) in place. FIG. 9A shows a portion of the circuit (900) prior to thermoforming. The circuit (900) includes a substrate (300), a number of electrodes (305-1, 305-2) formed on one surface of the substrate (300), and two flag extensions (330-1, 330-2).

The first flag extension (330-1) extends from the right side of the circuit and includes two through apertures (315-1, 315-2). The second flag extension (330-2) includes a single through aperture (315-3). Any or all of these through apertures (315) could be used for alignment purposes during manufacturing of the implantable lead (901, FIG. 9B). For example, if the electrodes (305) are formed on a first side of the circuit (900), the traces (325, FIG. 9B) may be formed on an opposite side of the circuit (900). The apertures (315) could be used to align the circuit (900) with the manufacturing machinery when the circuit (900) (or tray of circuits) is flipped over to form the traces (325).

As discussed above, the apertures (315) may also be used to align and secure the circuit (900) during processes such as thermoforming and liquid injection molding. Each of these processes can potentially produce moderate amounts of stress on the circuit. Pins or other alignment elements passing through apertures in the flag extensions can prevent undesirable motion of the circuit. The apertures shown in the figures are illustrated as being circular. Apertures with a variety of other shapes could be used. Additionally or alternatively, there may be a number of other features that could be used for alignment. For example, the flag extensions could have a dog bone shape that is fitted into a corresponding cavity to secure the circuit. In other examples, the flags may be pinched between two fixtures to secure the circuit in place, with one fixture above the circuit and one fixture below the circuit to pinch the thickness of the circuit between them. This pinching action does not require the flag extensions to have any particular geometry.

FIG. 9B is a cross section of an implantable lead (901) taken from line B-B of the circuit (900) after it has been thermoformed and the flexible body (420) has been formed. This cross section shows that the first flag extension (330-1) is now extending into the interior of the flexible body (420). This may be accomplished in a variety of ways. For example, the first flag extension (330-1) may be thermoformed into the desired shape (backward/inward at an acute angle) during the thermoforming operation. The second flag extension (330-2, FIG. 9A) is used as an alignment and stabilization aid during the thermoforming process. The circuit (900, FIG. 9A) is then placed into the liquid injection mold, with the second flag extension (330-2) again providing alignment and stabilization. The silicone is injected into the liquid injection mold and surrounds the first flag extension (330-1). The silicone flows through the apertures (315-1, 315-2). This provides a mechanical overlock that secures the first flag extension (330-1) in place. At this point, the first flag extension (330-1) portion of the circuit is secure in the flexible body (420). In some designs the use of flag extensions to provide mechanical overlooking may not be necessary. In other implementations, the flag extensions could be spaced along the electrode array and/or the lead body to secure the circuit in the flexible body.

After the implantable lead is formed, the flag extensions (such as 330-2) that were used only for alignment and anchoring during the manufacturing process can be removed. As shown in FIG. 9B, the second flag extension (330-2) has been removed. Removal of these flag extensions may be accomplished in a variety of ways, including cutting the flag extensions using mechanical force (such as scissors or a knife) or using a laser or other suitable technique. In one example, the flag extensions are removed with a laser at the same time that the laser removes silicone flash from the surface of the electrode.

Figure 10:
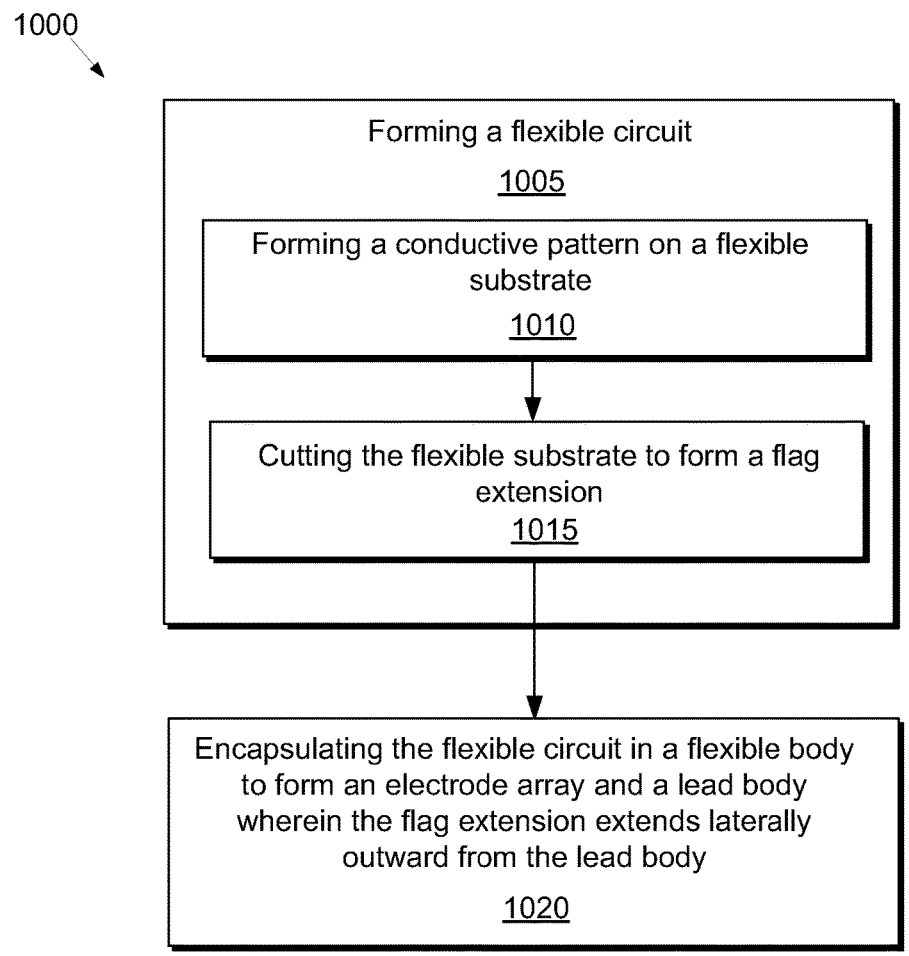
FIG. 10 is a flowchart of a method for forming an implantable lead with flag extensions, according to one example of principles described herein.

FIG. 10 is a flow chart of a method (1000) for forming an implantable cochlear lead. The method includes forming a flexible circuit (step 1005) by forming a conductive pattern on a flexible substrate (step 1010) and by cutting the flexible substrate to form a flag extension (step 1015). The flexible substrate is then encapsulated in a flexible body to form an electrode array and a lead body wherein the flag extension extends laterally outward from the lead body (step 1020).

The first portion of the flag extensions that extend out of the flexible body may form anchor points that may be attached to surrounding biological tissue in a variety of ways. For example, the flag extensions may be anchored by inserting a bone screw through an aperture in the flag extension and into tissue surrounding the cochlear lead. Additionally or alternatively, the flag extensions may be anchored by inserting a suture through the aperture and into tissue surrounding the cochlear lead. In some examples, the flag extension may be adapted to be secured to biological tissue and be used as an insertion depth marker. For example, the flag extension may be secured to biological tissue by passing a suture or other anchor through an aperture in the flag extension and radiopaque material may be formed around the aperture.

In some examples, the flag extensions may include an electrical contact pad that is connected to a trace. A separate conductive body may be placed over the contact pad and electrically connected with the contact pad. For example, this conductive body may be a ring electrode that acts in conjunction with other electrodes in the electrode array. For example, the ring electrode may be a ground electrode.

As described above, there may be multiple apertures in a single flag extension and multiple flag extensions. These apertures may serve a number of purposes including alignment during subsequent manufacturing operations by inserting an alignment pin through the aperture in the first flag extensions. These subsequent manufacturing operations may include thermoforming, liquid injection molding, lithography, cutting, or other operations.

The method described above is only one example. A variety of other methods could be used. For example, the steps in the method could be reordered, new steps could be introduced, steps could be combined, or various steps could be removed.

In summary, an implantable lead includes a substrate and an electrically conductive substrate disposed on the substrate to form a flexible circuit. The substrate may have a single layer or multiple layers. Each of these layers may be formed from thermoformable material or non-thermoformable material. In some instances, the substrate may include a flexible nonthermoformable material bonded to a thermoformable thermoplastic material. When the substrate includes one or more layers of thermoformable material such as a thermoplastic layer, the substrate may be thermoformed into a predetermined geometry.

The flexible circuit includes a proximal end adapted to electrically connect to an implantable processor as shown in FIG. 2B and a distal portion adapted to stimulate a cochlear nerve. The distal portion may be an electrode array adapted to be inserted into the cochlea (e.g. 195, FIG. 2B), or an electrode array that is adapted to directly stimulate the auditory nerve from outside the cochlea. A lead body (e.g. 190, FIG. 2B) extends from the proximal end to the distal portion and connects the processor to the distal portion. The lead body includes plurality of electrical traces adapted to carry electrical signals from the proximal end to the distal portion. One or more flag extensions (e.g. 504, FIG. 5B; FIG. 7A, 330-7) are formed in the substrate and extend laterally outward from a longitudinal axis of the lead body.

Portions of the flexible circuit may be encapsulated. The flag extension(s) may or may not be encapsulated. As discussed above, the flag extensions may include a through hole for receiving a suture and/or a radiopaque material. The flag extension may be adapted to be fixed to tissues proximal to the lead body. In some examples a flag extension may also serve as a depth marker adapted to show a target insertion depth of the implantable lead into biological tissue. For example, the depth marker may be thermoformed to lie flat against tissue at a surgical opening in the cochlea when the electrode array is inserted at the target insertion depth (see e.g. FIG. 8).

The preceding description has been presented only to illustrate and describe examples of the principles described. This description is not intended to be exhaustive or to limit these principles to any precise form disclosed. Many modifications and variations are possible in light of the above teaching.

What is claimed is:

1. An implantable lead comprising:
    a substrate; and
    an electrically conductive material disposed on the substrate to form a flexible circuit, the flexible circuit comprising:
        a proximal end to electrically connect to an implantable processor;
        a distal portion comprising an electrode array arranged to stimulate a cochlear nerve to induce hearing;
        a lead body extending from the proximal end to the distal portion, the lead body having a longitudinal axis and comprising a plurality of electrical traces adapted to carry electrical signals from the proximal end to individual electrodes of the electrode array of the distal portion, wherein the electrical traces and electrodes are disposed on opposite sides of the substrate; and
        a flag extension formed in the substrate and extending laterally outward from the lead body longitudinal axis, wherein the flag extension comprises a depth marker that indicates a target insertion depth of the lead into the cochlea.

2. The lead of claim 1, further comprising flexible encapsulant encapsulating at least a portion of the flexible circuit.

3. The lead of claim 2, wherein the flag extension is not encapsulated by the flexible encapsulant.

4. The lead of claim 2, wherein the flag extension is encapsulated by the flexible encapsulant.

5. The lead of claim 1, wherein the flag extension comprises a through hole for receiving a suture.

6. The lead of claim 1, wherein the substrate comprises a thermoplastic.

7. The lead of claim 6, wherein the flag extension is thermoformed from the thermoplastic of the substrate into a predetermined geometry.

8. The lead of claim 6, wherein the substrate further comprises a flexible non-thermoformable material bonded to the thermoplastic.

9. The lead of claim 1, wherein the flag extension further comprises an electrode.

10. The lead of claim 1, wherein the flag extension prevents further advancement of the implantable lead into biological tissue.

11. The lead of claim 1, wherein the flag extension comprises a radiopaque material.

12. The lead of claim 10, wherein the depth marker is thermoformed to lie flat against tissue at a surgical opening in the cochlea when the electrode array is inserted at the target insertion depth.

13. An implantable lead comprising:
    a flexible circuit having a distal end and a longitudinal axis, the flexible circuit comprising:
        a substrate; and
        an electrically conductive material disposed on a portion of the substrate forming:
            an electrode array on the distal end, the electrode array comprising a plurality of electrodes adapted to stimulate a cochlear nerve; and
        a lead body electrically coupled to the electrode array and extending proximally therefrom;
    wherein the substrate has a plurality of flag extensions formed therein, proximal of the electrode array, extending outwardly from the longitudinal axis, and adapted to be affixed to tissue and when affixed to the tissue, the plurality of flag extensions maintain a curvature in the lead body.

14. The lead of claim 13, wherein the plurality of flag extensions consists of three flag extensions.

15. The lead of claim 13, wherein each of the flag extensions extends from a common side of the lead body and has a common shape and a common orientation relative to the lead body.

16. The lead of claim 13, wherein each of the flag extensions has a surface and comprises an aperture orthogonal to its surface.

17. An implantable lead comprising:
    a substrate; and
    an electrically conductive material disposed on the substrate to form a flexible circuit, the flexible circuit comprising:
        a proximal end to electrically connect to an implantable processor;
        a distal portion comprising an electrode array arranged to stimulate a cochlear nerve to induce hearing;
        a lead body extending from the proximal end to the distal portion, the lead body having a longitudinal axis and comprising a plurality of electrical traces adapted to carry electrical signals from the proximal end to individual electrodes of the electrode array of the distal portion, wherein the electrical traces and electrodes are disposed on opposite sides of the substrate; and a flag extension formed in the substrate and extending laterally outward from the lead body longitudinal axis such that a plane of the flag extension is orthogonal to the longitudinal axis of the lead body.

18. The lead of claim 17, wherein the flag extension comprises an aperture configured to receive an anchor for anchoring the electrode array in place.

19. The lead of claim 17, wherein the flag extension comprises a marker flag to increase visibility of the flag extension.

* * * * *